United States Patent
Parel et al.

[11] Patent Number: 6,154,671
[45] Date of Patent: Nov. 28, 2000

[54] DEVICE FOR THE INTRAOCULAR TRANSFER OF ACTIVE PRODUCTS BY IONTOPHORESIS

[75] Inventors: Jean-Marie Parel, Miami Shores, Fla.; Francine Behar, Paris, France

[73] Assignee: Optisinvest, Curacao, Netherlands Antilles

[21] Appl. No.: 09/225,206

[22] Filed: Jan. 4, 1999

[30] Foreign Application Priority Data

Jan. 5, 1998 [FR] France ................... 98 00009

[51] Int. Cl.[7] ................ A61N 1/30; A61M 31/00
[52] U.S. Cl. ........................ 604/20; 604/521
[58] Field of Search .................. 604/19, 20, 501, 604/521, 289, 294; 607/53, 54, 141; 424/427

[56] References Cited

U.S. PATENT DOCUMENTS

| | | | |
|---|---|---|---|
| 551,880 | 12/1895 | Wilcox | 604/20 |
| 2,525,381 | 10/1950 | Tower | 604/20 |
| 3,122,137 | 2/1964 | Erlanger | 604/20 |
| 4,564,016 | 1/1986 | Maurice et al. | |
| 4,678,466 | 7/1987 | Rosenwald | |
| 4,955,378 | 9/1990 | Grasso | 604/20 |
| 5,053,000 | 10/1991 | Booth et al. | 604/20 |
| 5,053,001 | 10/1991 | Reller et al. | 604/20 |
| 5,174,304 | 12/1992 | Latina et al. | 604/20 |
| 5,472,436 | 12/1995 | Fremstad | |
| 5,522,864 | 6/1996 | Wallace et al. | 607/53 |
| 5,879,323 | 3/1999 | Henley | 604/20 |
| 6,001,088 | 12/1999 | Roberts et al. | 604/501 |

FOREIGN PATENT DOCUMENTS

| | | | |
|---|---|---|---|
| 0654254 | 3/1979 | Russian Federation | 604/20 |
| 1342500 | 10/1987 | Russian Federation | 604/20 |
| 90/11054 | 10/1990 | WIPO | 604/20 |

OTHER PUBLICATIONS

Sarraf et al., D., "The Role of Iontophoresis in Ocular Drug Delivery", Journal of Ocular Pharmacology, vol. 10, No. 1, 1994, pp. 69–81.

*Primary Examiner*—Sharon Kennedy
*Attorney, Agent, or Firm*—Oblon, Spivak, McClelland, Maier & Neustadt, P.C.

[57] ABSTRACT

A device for transferring a medicament into the eyeball by iontophoresis. A reservoir holding the active product is applied to a patient's eye. The reservoir has at least one active surface electrode facing the eye tissue lying at the periphery of the cornea. The reservoir also has a return electrode and a current generator. The return electrode is in contact with the patient's partly closed eyelids.

30 Claims, 5 Drawing Sheets

DEVICE FOR THE INTRAOCULAR TRANSFER OF ACTIVE PRODUCTS BY IONTOPHORESIS

BACKGROUND OF THE INVENTION

1. Field of the Invention

The present invention relates to a device for the intraocular transfer of active products by iontophoresis.

2. Discussion of the Background

Iontophoresis is a technique which was proposed in 1747 by Verrati and consists in the administration, in particular of medicaments, into the body through the tissues using an electric field involving a small potential difference. The active electrode, which is in contact with the medicament, is arranged at the site to be treated while a second electrode, intended to close the electric circuit, is placed at another site on the body.

The electric field facilitates the migration of the active products, which are preferably ionized. This technique is commonly used for treating skin diseases, and for this purpose there are a variety of devices available on the market.

Iontophoresis applied to treatment of the eye has been the subject of a number of animal experiments and a few clinical tests, using a variety of devices.

Known devices employ a pad which is impregnated with a solution containing a medicament and is in contact with the surface of the cornea and the sclera. Other devices employ a cup or a pipette. A device employing a cup is, for example, described in American patent U.S. Pat. No. 4,564,016 (David M. Maurice). In this patent, the medicament is administered in quasi-point form through the sclera.

In general, the authors find poor reproducibility in their results, which they attribute either to the existence of differences between the animals which are tested, or to unexplained biological phenomena. Furthermore, some operating techniques involve the use of an active electrode of very small area with a very high current density, which increases the risk of damage caused to the tissues, it being possible for this damage to extend to the presence of burns. This is the case, in particular, with the device described in the aforementioned U.S. Pat. No. 4,564,016, which advocates a current density which is at least 50 mA/cm$^2$ and may even be as much as 2000 mA/cm$^2$.

Some experiments have been carried out with alkaline solutions whose high pH results in local tissue damage. For example, the article by T. T. Lam et al. "Intravitreal Delivery of Ganciclovir in Rabbits by Transscleral Iontophoresis" published in the Journal of Ocular Pharmacology 10(3) p. 571–575 (1994) describes the point administration of a solution whose pH of 10.8 is out of the question except in the laboratory.

The article by F. Behar-Cohen et al., entitled "Iontophoresis of Dexamethasone in the Treatment of Endotoxin-Induced-Uveitis in Rats" in the journal Experimental Eye Research, 1997-65 p. 533–545 (October 1997), relates to transcorneoscleral iontophoresis carried out on rats with a view to the treatment of uveitis, that is to say a condition affecting the uvea. According to this technique, the medicament diffuses essentially through the cornea, then diffuses into the eye media.

In practice, owing to the lack of reproducibility of the experimental results generally obtained and, above all, the description of burns and necrosis to the tissue where the iontophoresis devices are applied, transocular iontophoresis has remained at the laboratory stage and has not yet been accepted as a method of treating patients.

SUMMARY OF THE INVENTION

The invention relates to a device for transferring at least one active product into the eyeball by iontophoresis, which makes it possible to carry out ambulatory treatments reproducibly.

The invention thus relates to a device for transferring at least one active product into the human eyeball by iontophoresis, comprising a reservoir of active product, for example of medicament, which can be applied to a patient's eye, at least one active electrode arranged in the reservoir, a passive electrode and a current generator, characterized in that one said active electrode is a surface electrode arranged facing eye tissues lying at the periphery of the cornea. The regions of the eyeball facing the electrode are the corneoscleral limbus, the conjunctiva and/or the sclera and/or the ciliary body and/or the root of the iris and/or the pars plana and/or the anterior vitreous humour and/or the nonfunctional undetachable retina.

Given that the transfer takes place through one or more eye tissues lying at the periphery of the cornea over a wide application area, the reproducibility, transfer uniformity and efficacy are increased. These tissues become impregnated with the medicament (or active product) which may become concentrated there even though the concentrations in the eye media remain low. These concentrations do not reflect the intratissue medicament concentrations. The medicament is thus not eliminated rapidly by the replenishment of the eye liquids (aqueous humour AH and vitreous humour V).

Furthermore, given that the active product is not in contact with the cornea, this avoids the drawbacks of transcorneal iontophoresis and the risk of endothelial lesions, namely the existence after the intervention of sight problems connected either with endothelial lesions or with temporary epithelial lesions or with temporary deposits of active products, which cause blurred vision. The treatment is therefore a genuinely ambulatory one.

Lastly, since the treatment is carried out on a ring peripheral to the cornea, a cylindrical central region of the device can be left fully free, and the practitioner can therefore visually check the centred positioning of the device during the iontophoresis.

All the eye tissues can be treated: conjunctiva, cornea, sclera, iris, crystalline lens, ciliary body, choroidea, retina and optic nerve.

In accordance with the parameters chosen for the current (strength of the current, duration of the treatment), it will be possible for certain tissues to he more specifically targeted.

For an adult (nominal diameter of the cornea: 12 mm), the annular electrode or the electrodes in the form of annular sectors, which is or are made, for example, by electrolytic deposition, may have an internal diameter lying between 12.5 mm and 14 mm and an external diameter lying between 17 mm and 22 mm, which corresponds to an area lying between about 75 mm$^2$ and 250 mm$^2$, and preferably between 17 mm and 20 mm. The maximum diameter is chosen so as not to touch the functional retina. For a child whose eye has not reached adult size, the dimensions need to be adapted in proportion. In other words, and in the general case, the internal diameter di of the annular electrode or of the electrodes is greater than the diameter D of the cornea and less than or equal to 1.2 D, and the external diameter of the annular electrode or of the electrodes is greater than or equal to 1.4 D and less than or equal to 1.8 D, and preferably less than or equal to 1.7 D.

The current generator may be a constant-current generator with rated density less than 10 mA/cm$^2$, which includes a control device which makes it possible to apply the said constant current for a period of time of between 30 seconds and 10 minutes, and more particularly between 1 minute and 10 minutes.

The density of the constant current is advantageously adjustable between 0.1 mA/cm$^2$ and 5 mA/cm$^2$, for example between 0.2 mA/cm$^2$ and 5 mA/cm$^2$, or alternatively between 0.8 mA/cm$^2$ and 5 mA/cm$^2$.

The current may be applied progressively, for example during the initial seconds, which avoids the patient's reflex muscular reactions.

The current is advantageously delivered at a voltage lying between 1.5 V and 9 V, and preferably between 2 V and 8 V.

The concentration of the active product is arbitrary. It is in particular less than or equal to the saturation concentration of the active product in water. It is preferably greater than or equal to a threshold concentration beyond which accummulation in some of the eye tissues followed by release to other tissues takes place.

The active product arranged in the reservoir has a pH which may advantageously lie between 6 and 8, and preferably between 7 and 7.6. It will be noted that, since the active product is not in contact with the cornea, the chosen pH may be substantially higher than indicated above, because the conjunctiva and the sclera are less susceptible both in terms of sensitivity and in terms of lesions to slightly acidic or basic pH values. The cornea must remain transparent. Any modification to the physiological conditions risks impairing its tissue characteristics, and therefore its transparency. The conjunctiva is a mucous membrane, and the sclera is a conjunctive tissue. These are two very resistant tissues whose function is not, in the application region of the treatment, directly involved in the transmission of photons to the retina. They are connective tissues.

The device preferably has a pumping device for circulating a solution of active product, for example a medicinal solution, through the reservoir. This makes it possible, on the one hand, to eliminate the gas bubbles which may be formed during the iontophoresis and, on the other hand, to keep the composition and the pH of the solution substantially constant throughout the treatment, and therefore to improve its reproducibility.

According to a first embodiment, the device has an annular reservoir having an annular electrode, which may define the bottom of the reservoir.

According to a second embodiment, the device has an annular reservoir having a plurality of compartments in the form of annular sectors and electrodes in the form of an annular sector, which may define the bottom of the annular sectors.

According to a third embodiment, the device consists of a corneal lens which is provided with a surface electrode on its internal face and in which a gel containing at least one active product is arranged, or which itself has a spongy structure and contains the active product (for example a cross-linked matrix).

Preferably, on an external face, the device includes a passive electrode which comes into contact with the patient's partially closed eyelid, which holds the device in place throughout the treatment. This also provides the advantage of electrical contact which is improved because it is in an aqueous environment.

BRIEF DESCRIPTION OF THE DRAWINGS

Other characteristics and advantages of the invention will become more clearly apparent on reading the following description, given by way of non-limiting example in conjunction with the appended drawings, in which.

DETAILED DESCRIPTION OF THE PREFERRED EMBODIMENTS

Figure 1:
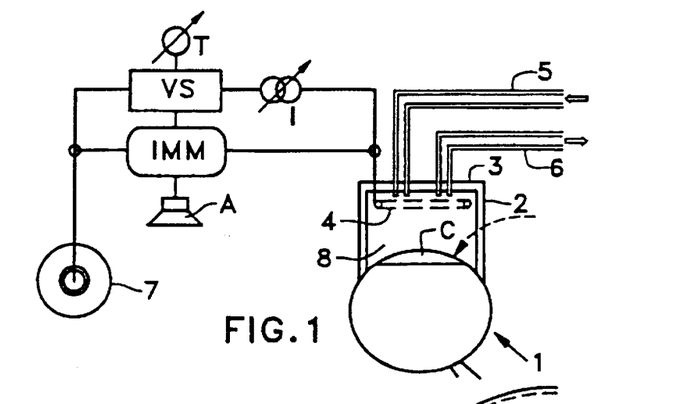
FIG. 1 represents a section of an example of a device described in the aforementioned article by F. Behar-Cohen et al.

FIG. 1 schematically represents the iontophoresis system employed in the context of the aforementioned article by F. Behar-Cohen et al. It includes a polymethyl methacrylate (PMMA) reservoir 8 defined by a cylindrical wall 2 and a bottom 3 in proximity to which a circular platinum electrode 4 is arranged. The reservoir 8, with a diameter of 6 mm, covers the cornea, the limbus and the first millimeter of the sclera of a rat. A feed tube 5 makes it possible to fill the reservoir 8 with a solution metered in a proportion of 1 mg of dexamethasone per ml of a pH 7 sterile saline solution, and a discharge tube 6 makes it possible to extract the air bubbles which are formed during the iontophoresis. Continuous circulation of the solution makes it possible to keep the pH of the solution in contact with the cornea constant.

A return electrode 7 is placed in contact with one of the rat's paws.

The system also includes a voltage source VS, and a current regulator I. A device IMM for measuring impedance makes it possible to detect any electrical discontinuity and trigger an alarm A. The quantity of charge delivered is displayed on the generator at the end of treatment and makes it possible to ensure reproducibility of the administered treatment.

The experiments were carried out with a current of 400 $\mu$A for 4 minutes, i.e. a density of 1.2 mA/cm$^2$ and a total charge of 0.12 coulomb i.e. 0.4 C/cm$^2$.

Figures 2A, 2B:
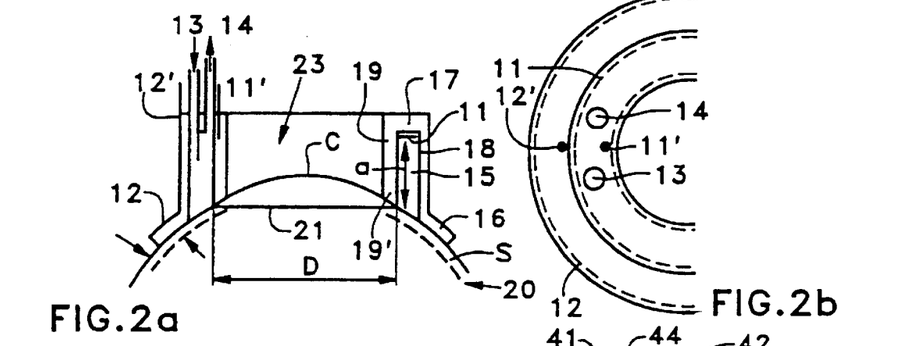
FIGS. 2a to 2c respectively represent a section, a plan view and a perspective view of an example of a device according to the invention FIGS. 3a, 3b and 3c respectively represent a section, a plan view and a perspective view of a device according to the invention for administering three active products, for example three medicaments
Figure 2C:
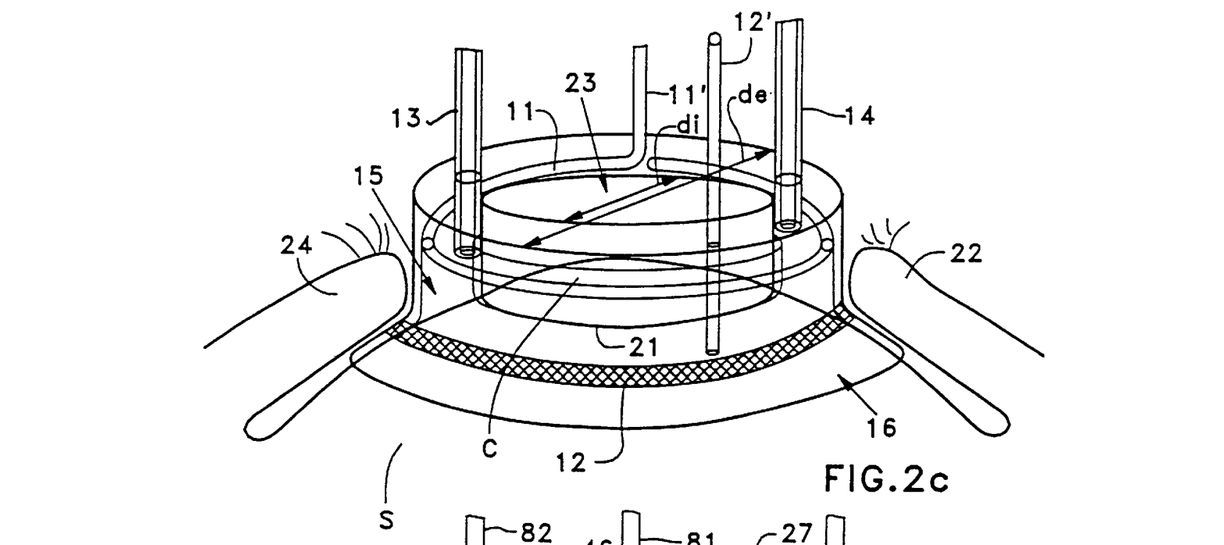

The device according to the invention, an embodiment of which is represented in FIGS. 2a and 2b, makes it possible to transfer active product, for example a medicament, essentially through at least one eye tissue.

The active electrode is advantageously placed at a distance a from the surface of the patient's eye which is sufficient to avoid a short-circuit, or to avoid it coming accidentally into contact with the eye. This distance a is preferably at least equal to 4 mm.

The device may be made of PMMA or preferably silicone, for example PDMS with a Shore hardness of 20, for a better seal at the eye. Another biocompatible material which may be used is polyurethane, in particular a polyurethane which is hydrophilic in order to improve adhesion and the elimination of bubbles.

The device 10 has an annular wall 17 and two cylindrical side walls, an inner one 19 and an outer one 18, defining an annular region 15 which forms a reservoir for an active solution, for example a medicinal solution, to be administered by iontophoresis at the periphery of the cornea C of an eye 20 to be treated. The end of the wall 18 adjacent to the wall 17 rests through a frustoconical edge 16 on the sclera S, and the end of the wall 19 adjacent to the wall 17 rests through a frustoconical zone 19' on the perimeter of the cornea C so that only a region which is peripheral to the cornea C and has one or more eye tissues is exposed to the medicinal solution contained by the reservoir 15. An annular active electrode 11 borders the wall 17. Two conductive connections 11' and 12' make it possible to electrically connect the active electrode 11 and the return electrode 12, which is advantageously arranged on the external face of a ring 16, so that the patient's partially closed eyelid can come into contact with the electrode 12 and thus close the circuit.

Alternately, the return electrode may be separate and arranged on the patient's forehead, close to the eye to be treated. In this case as well, the patient's eyelid may rest on the ring 16 in order to hold the device in place.

Openings 13 and 14 formed in the wall 17 make it possible to fill the reservoir 15 and/or circulate the medicinal solution.

The plane annular electrode 11 preferably covers the entire surface of the wall 17 which defines the bottom of the annular reservoir 15. Only partial coverage is admittedly envisageable, but can only unfavourably influence the efficacy of the treatment. Whatever the case, the reservoir 15 must not cover the region of the cornea C.

Figures 3A, 3B:
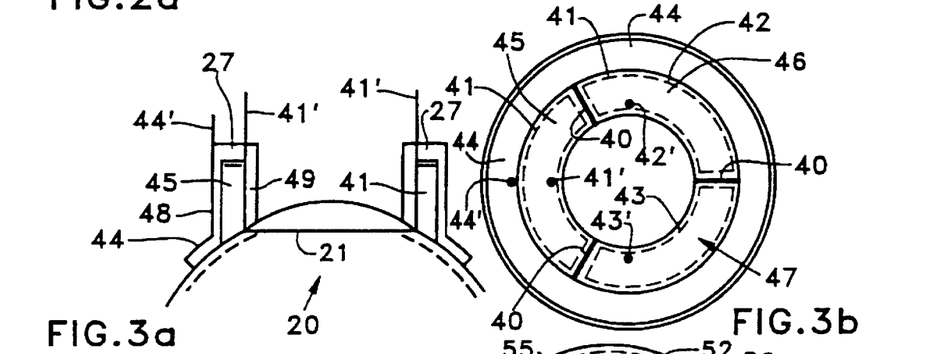
Figure 3C:
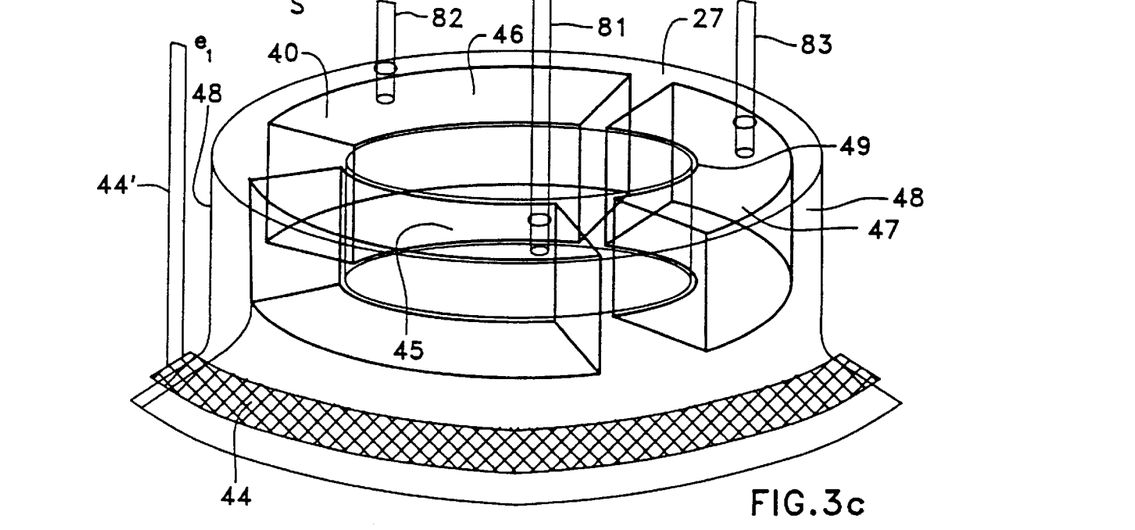

The device represented in FIGS. 3a, 3b and 3c makes it possible to administer a plurality of active products, for example medicaments, here three of them, in liquid or gel form, which are each arranged in one of three cavities in the form of an annular sector 45, 46 and 47 each of which is provided with a respective active electrode 41, 42 and 43. The device includes an annular wall 27, and two cylindrical walls, an inner one 49 and an outer one 48, and the sectors are defined by separating walls 40. It is placed on the patient's eye in the same way as the device represented in FIGS. 2a and 2b. Conductive connections 41', 42' and 43' pass through the wall 27 to electrically supply the active electrodes 41, 42 and 43.

Figure 4:
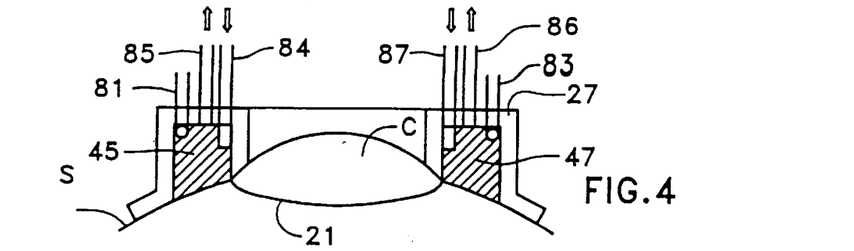
FIG. 4 represents a section of a variant of the device according to FIGS. 3a to 3c FIGS. 5a to 5b represent a device according to the invention, in the form of a meniscus intended for administering three active products, for example three medicaments, in gel form FIGS. 6a to 6c respectively represent a perspective view, a section and a partial section of a device of the meniscus type according to the invention

The device represented in FIG. 4 is distinguished by the presence of tubes for circulating liquid which are present for each cavity 45, 46 and 47. The drawing shows the tubes 84, 85 and 86, 87 corresponding to the cavities 45 and 46.

Figures 5A, 5B:
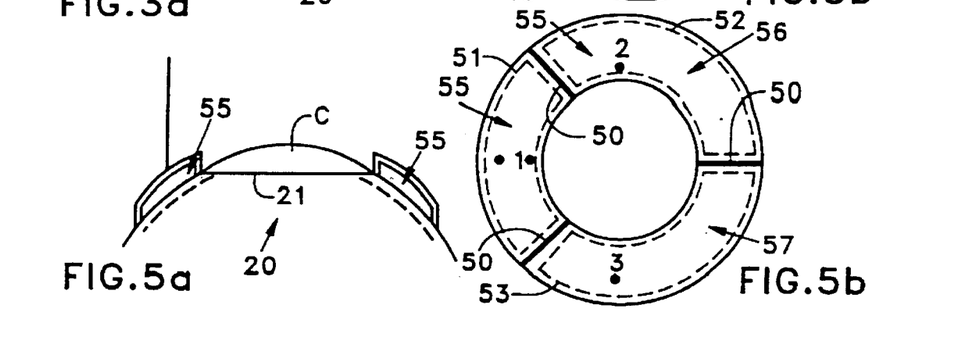
Figures 6A, 6B, 6C:
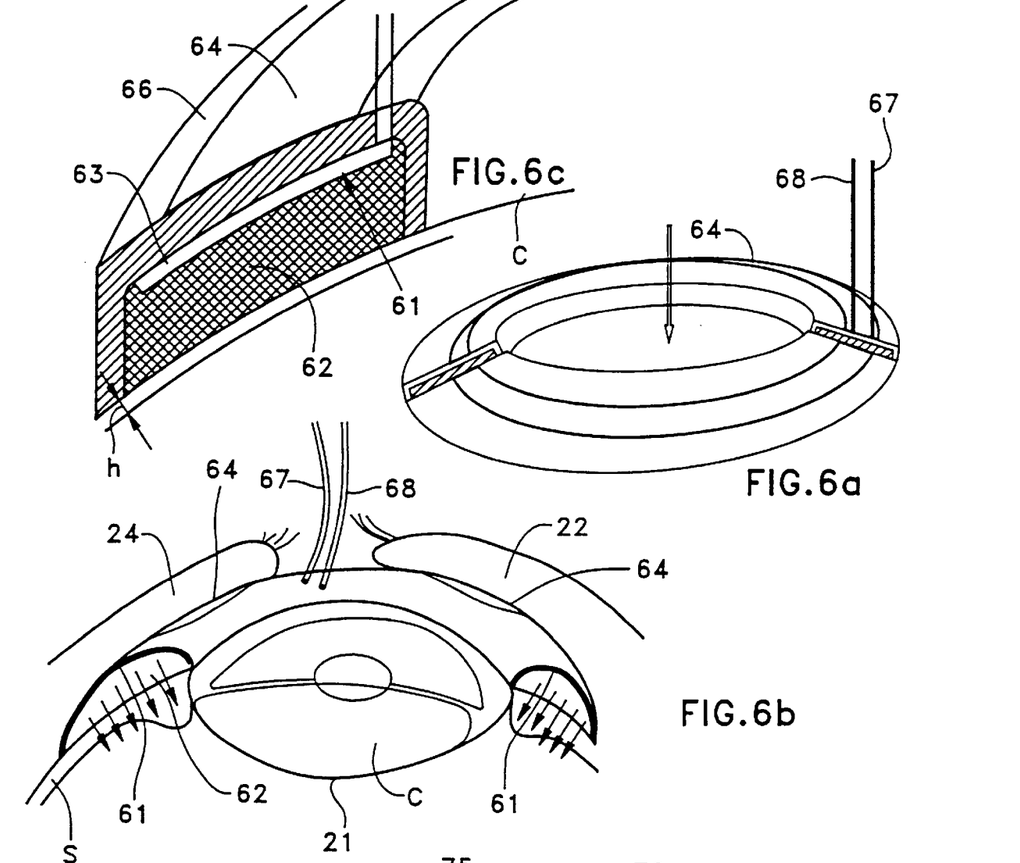

The device represented in FIGS. 5a and 5b is a meniscus in the form of a ring. It has three reservoirs 55, 56 and 57 each of which is intended to hold a medicinal gel or a porous material, such as a sponge, impregnated with an active product, for example a medicament. A respective active electrode 51, 52 and 53 is associated with each reservoir. The reservoirs 55 in the form of sectors are defined by separating walls The device represented in FIGS. 6a to 6c is a flat meniscus in ring form made of a material which may be that of a corneal lens. The cylindrical central space 63 is left free and, as with the other embodiments, allows a visual check of the centred positioning of the device. An electrode 61, for example formed by electrolytic deposition, covers the slightly concave internal face 63 of the bottom of the annular cavity 62. A return electrode 64, for example formed by electrolytic deposition, covers the perimeter of the convex external face 66 of the bottom of the annular cavity 62, so as to allow return electrical contact through at least one of the patient's closed eyelids 22, 24. The routing of the electrical contact wires 67, 68 is arranged in such a way as to allow them to exit between the eyelids.

The device according to the invention is generally suitable for simple molecules or for molecular assemblies used as an active product (for example medicaments and/or peptides and/or proteins and/or gene fragments) whose molecular mass is less than 100 kilodaltons.

Operation is carried out with a direct current which is constant and regulated with a current density that does not exceed 10 mA/cm$^2$. This current density can advantageously be adjusted between 0.1 mA/cm$^2$ and 5 mA/cm$^2$, and for example between 0.2 mA/cm$^2$ and 5 mA/cm$^2$. The preferred value range lies between 0.8 mA/cm$^2$ and 5 mA/cm$^2$. The treatment time may lie between 30 seconds and 10 minutes. It may in particular lie between 1 minute and 10 minutes.

For a human being, the diameter of the cornea (with limbus) is about 12 to 13 mm with an ora serrata about 18 mm in diameter.

By way of example, for treating adults, use may be made of an annular electrode or a plurality of electrodes in the form of ring sectors having an internal diameter lying between 12.5 and 14 mm and an external diameter lying between 17 mm and 22 mm, which corresponds to an area lying between 75 mm$^2$ and 250 mm$^2$, and preferably lying between 17 mm and 20 mm. The current may, in this case, for example be 400 $\mu$A and be applied for 4 minutes.

It will be noted that the arrangement of the active electrodes, namely of the surface electrodes arranged facing the region(s) to be treated, makes it possible to associate with a constant current a current density which is itself constant and uniform over the entire area of the region to be treated.

This presents several advantages.

Firstly, it prevents the current density from being able to locally reach high values in certain zones of the region to be treated, and therefore giving rise to undesirable side effects.

Furthermore, the uniformity of the current density in the region to be treated has the effect that the penetration of the active product or products, for example of the medicaments, is also uniform over the region to be treated.

Whatever the case, the electrode does not face the functional retina.

In the scope of the present invention, at least one active product, for example a medicament, is administered via the tissues which allow the better penetration of the active product, in the anterior and posterior segment: the corneoscleral limbus, the conjunctiva, the sclera, the ciliary body, the root of the iris, the pars plana, the anterior vitreous humour, the choroidea and the nonfunctional undetachable retina.

The absence of contact with the cornea avoids any risk of physical and chemical lesion and, in particular, temporary or permanent eye problems following the treatment, and it also makes it possible to leave free a central space 23 allowing the practitioner to check the positioning of the instrument throughout the treatment.

Furthermore, it is found that beyond a certain concentration of active product, which varies depending on the nature of the active product, the active product accummulates in certain tissues of the eye 'sustentacular space, sclera, suprachoroid space and, to a lesser extent, iris I and ciliary body CC) before being progressively released to other tissues (choroid CH, retina RET), thus increasing the action time (half-life before elimination of the active product).

Figure 8A:
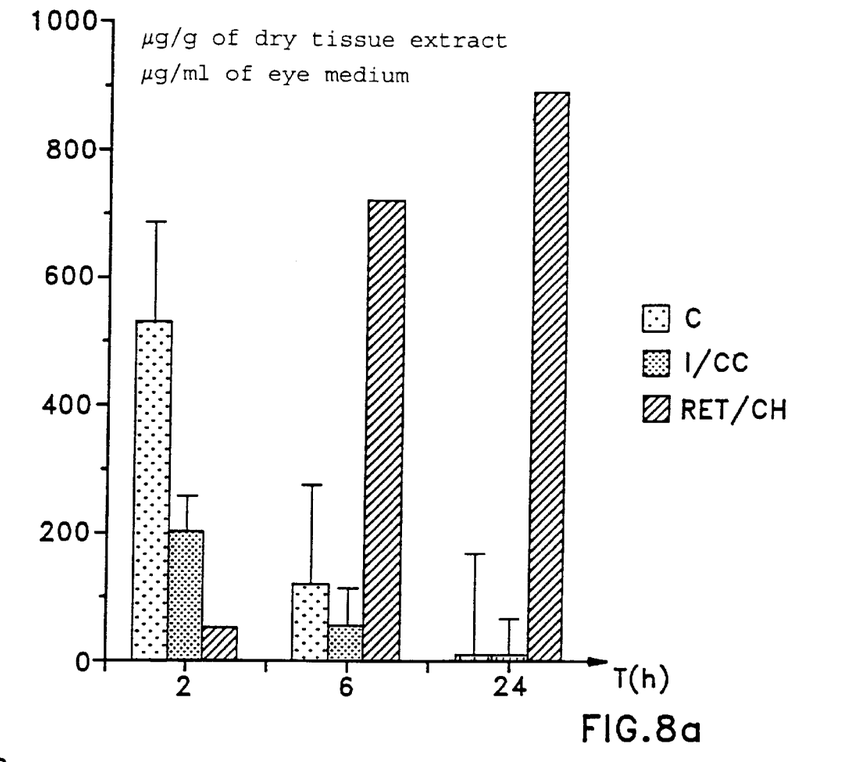
FIGS. 8a and 8b are results of a test carried out on rabbits, with the concentration in $\mu$g/g of dry tissue and in $\mu$g/ml for the eye media on the ordinate, and the time in hours on the abscissa
Figure 8B:
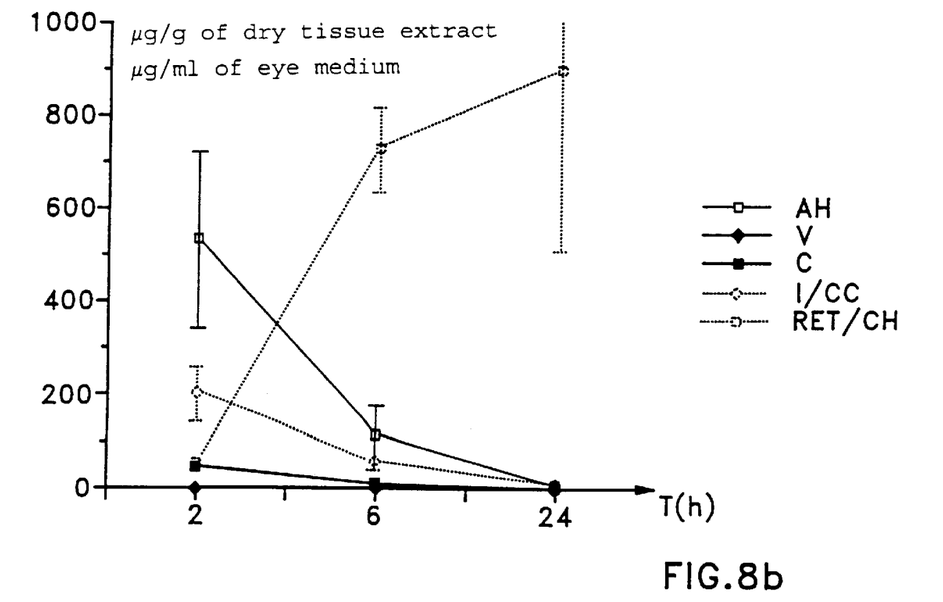

This phenomenon is illustrated by the appended curves (FIGS. 8a and 8b) obtained on the basis of experiments carried out on rabbits with methylprednisolone hemisuccinate (150 mg/ml, 2 mA). With a 62.5 mg/ml strength solution, the release effect is not observed. The concentration threshold which allows release is about 100 mg/ml.

The device according to the invention may be axisymmetric, but it is preferable for it to be substantially oval in order to accommodate, on the one hand, the presence of the eyelids and, on the other hand, the slightly oval profile of the cornea.

Figure 7:
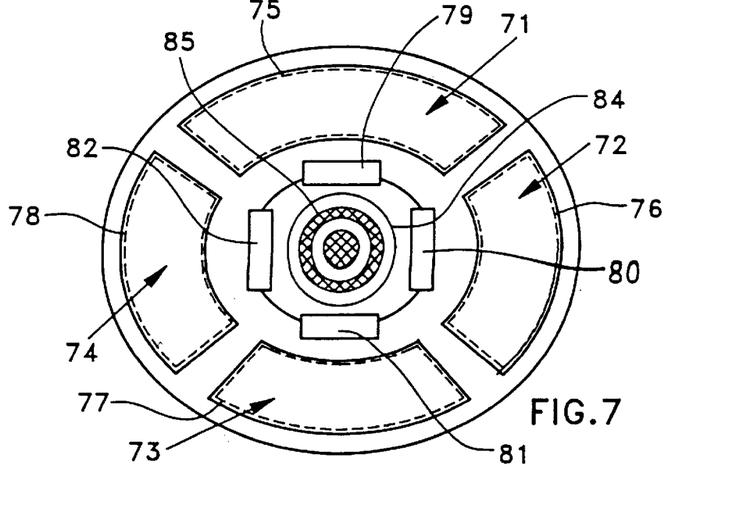
FIG. 7 represents a preferred embodiment of a device intended for administering a plurality of active products, for example medicaments

The device represented in FIG. 7 has a cavity with an elliptical external profile of 20 mm focal axis parallel to the closure line of the eyelids, and of 18 mm minor axis.

An elliptical internal profile of the treatment cavity may, for example, have a major axis which is parallel to the closure line of the eyelids and is equal to 13.5 mm, and a minor axis which is perpendicular to this line and is equal to 12.5 mm.

The device represented in FIG. 7 has four cavities 71 to 74 each of which has an active electrode 75 to 78 supplied by an individual electronic circuit 79 to 82 which is similar to the one represented in FIG. 1 and which is integrated in the device. The electronic circuits are supplied by a battery 84 constituting the voltage generator VS, and include a constant-current source I regulated to a chosen value, and a timer T allowing the desired treatment time to be set. Alternatively, all the circuits may be arranged on a single integrated circuit, or alternatively the functions may be distributed over several internal circuits connected by a bus 85.

It will be noted that the reservoir may be oval or, alternatively, have an elongate shape, for example an elliptical shape.

The reservoir and/or the active electrode may be annular.

It is also within the scope of the present invention for the reservoir to have an internal diameter di with $D<di \leq 1.2\,D$, D denoting the diameter of the cornea, and an external diameter de with $1.4\,D \leq de \leq 1.8\,D$, and preferably $1.4\,D \leq de \leq 1.7\,D$.

Figures 9, 10:
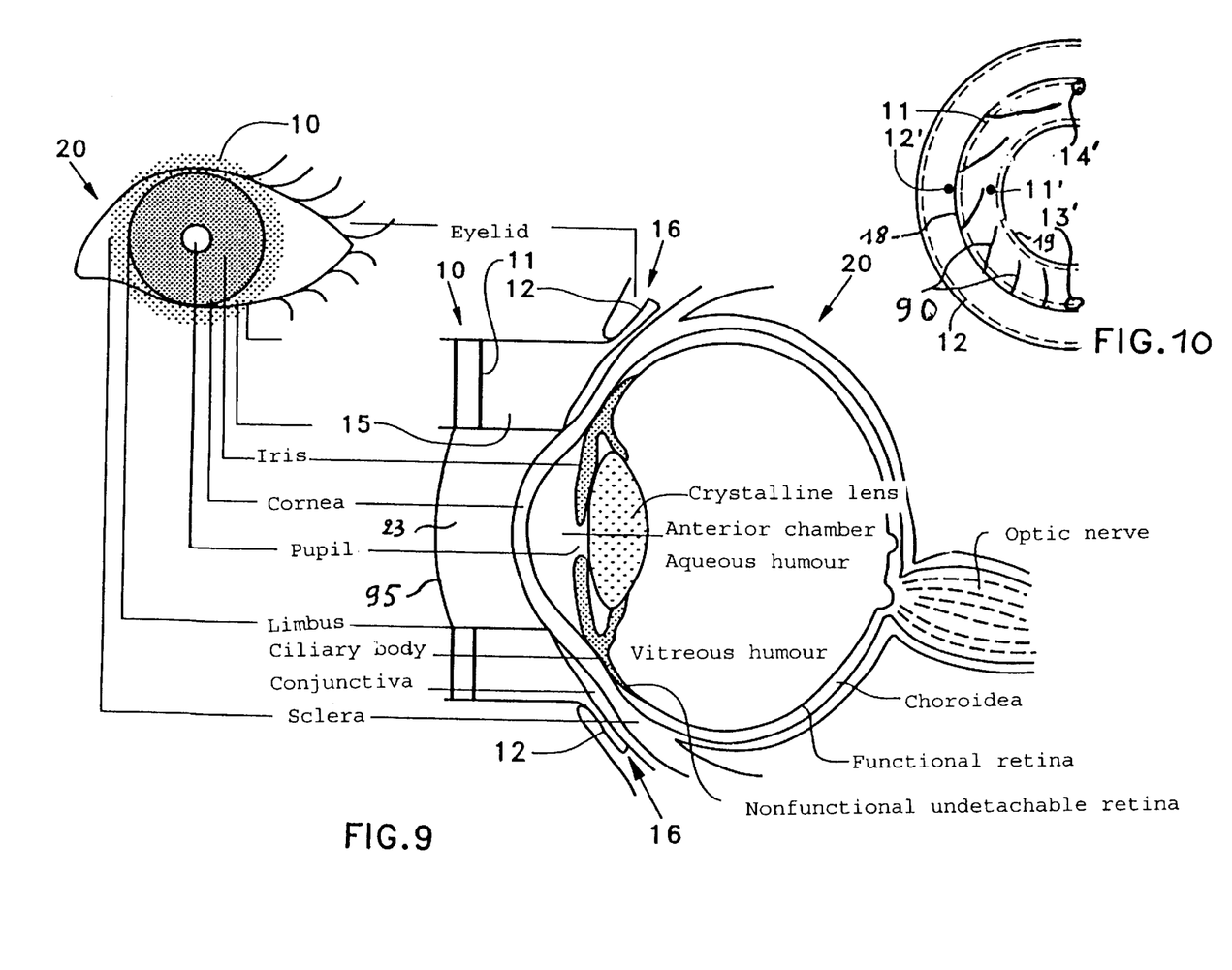
FIG. 9 represents a device according to the invention as fitted on an eye to be treated and FIG. 10 represents a plan view of a preferred alternative embodiment of the invention.

The device may be held in place using a suction device producing a vacuum lying between 35 mm Hg and 100 mm HG, and preferably of the order of 50 mm Hg. This vacuum may in particular be generated using a preferably transparent diaphragm 95 (FIG. 9) which closes off the external face of the central space 23, which makes it possible to create a vacuum therein by suction. This vacuum may also be created by the practitioner if he presses on the diaphragm 95 to flush the air from the central space, which will cause a said vacuum after release. Since the depressurizing diaphragm 95 is transparent, the practitioner can check the positioning of the instrument during the treatment, by virtue of the central space 23.

The active product may be injected through a syringe or, alternatively, from a container of active product adjacent to the device.

When the device is made of a flexible material, which is favourable in terms of fitting and sealing, the external 18 and internal 19 cylindrical walls will tend to come into contact with one another.

In order to overcome this, fins 90 are provided, for example plane radial fins which preferably extend from one of the cylindrical walls (18 or 19) while remaining spaced apart from the other wall (19 or 18) when the device is inactive. In order to facilitate the discharge of air bubbles, the active solution is injected into the reservoir 15 through an inlet 13' (see FIG. 10) lying in the lower part ("6 o'clock position") of the device when placed on the eye of a patient whose head is tilted backwards, and an opening 14' for discharging the bubbles is provided in the upper part ("12 o'clock position"). In order to assist in discharge of the bubbles, the fins 90, which in the example which is represented extend from the wall 18, are curved and are convex in the direction of the inlet opening 13'.

We claim:

1. A device for transferring at least one active product into an eyeball by iontophoresis, comprising a reservoir configured to receive an active product and having an internal wall, an external wall, and an end wall bridging the internal wall and the external wall, the internal wall and the external wall being annular and having a free end configured to be applied to an eyeball, said device further comprising at least one active electrode arranged in the reservoir, a passive electrode and a current generator, wherein the at least one active electrode is a surface electrode arranged on an interior surface of the end wall and wherein the internal wall has an outer diameter that is configured to be at least equal to a predetermined diameter, whereby the predetermined diameter represents a diameter of a human cornea.

2. A device according to claim 1, characterized in that the reservoir and/or the active electrode is annular.

3. The device according to claim 1, wherein the current generator is a constant-current generator with rated current density less than 10 mA/cm$^2$, and wherein the current generator includes a control device which is configured to apply a constant current for a period of time in a range of 30 seconds to 10 minutes.

4. The device according to claim 3, wherein the period of time is in a range from 1 minute to 10 minutes.

5. The device according to claim 3, wherein the current density is in a range from 0.1 mA/cm$^2$ to 5 mA/cm$^2$.

6. The device according to claim 5, wherein the current density is in a range from 0.2 mA/cm$^2$ to 5 mA/cm$^2$.

7. The device according to claim 1, wherein the current density is in a range from 0.8 mA/cm$^2$ to 5 mA/cm$^2$.

8. The device according to claim 1, wherein the reservoir and the at least one active electrode are annular.

9. The device according to claim 1, wherein the reservoir is configured to satisfy a relationship defined by $D<di \leq 1.2D$ and a relationship defined by $1.4D \leq de \leq 1.8D$, where D denotes the diameter of the human cornea, di denotes an internal diameter of the reservoir, and de denotes an external diameter of the reservoir.

10. The device according to claim 9, wherein the reservoir is configured to satisfy a relationship defined by $1.4D \leq de \leq 1.7D$.

11. The device according to claim 9, wherein the internal diameter is in a range of 12.5 mm to 14 mm, and the external diameter is in a range from 17 mm to 22 mm.

12. The device according to claim 11, wherein the external diameter is in a range from 17 mm to 20 mm.

13. The device according to claim 1, wherein the current is delivered at a voltage in a range from 1.5V to 9V.

14. The device according to claim 13, wherein the current is delivered at a voltage in a range from 2V to 8V.

15. The device according to claim 1, further comprising an active product positioned within the reservoir and having a pH in a range from 6 to 8.

16. The device according to claim 1, wherein the active product has a pH in a range from 7 to 7.6.

17. The device according to claim 1, further comprising a pumping device configured to circulate a medicinal solution through the reservoir.

18. The device according to claim 1, wherein the reservoir is annular, the reservoir having a compartment and an annular electrode.

19. The device according to claim 1, wherein the reservoir has an elongate shape.

20. The device according to claim 19, wherein the reservoir has an elliptical shape.

21. The device according to claim 1, wherein the reservoir contains at least one gel material impregnated with an active product.

22. The device according to claim 1, wherein the reservoir contains at least one porous material impregnated with an active product.

23. The device according to claim 22, wherein the at least one porous material is a sponge.

24. The device according to claim 1, further comprising a passive electrode on an external face of the device, whereby the passive electrode is configured to contact an internal face of a patient's at least partially closed eyelid.

25. The device according to claim 1, wherein the reservoir defines a central space whereby a practitioner can check a positioning of the device relative to a patient's eye.

26. A device for transferring at least one active product into an eyeball by iontophoresis, comprising an annular reservoir configured to receive an active product, the reservoir having an eyeball receiving portion and a plurality of compartments in the form of annular sectors, a plurality of active electrodes arranged in the reservoir in the form of annular sectors, a passive electrode and a current generator, wherein one of the plurality of active electrodes is a surface electrode arranged opposite the eyeball receiving portion.

27. The device according to claim 26, wherein the device is a flat meniscus.

28. A device for transferring at least one active product into an eyeball by iontophoresis, comprising an annular reservoir configured to receive an active product, the reservoir having an eyeball receiving portion, at least one active electrode arranged in the reservoir, a passive electrode and a current generator, wherein one of the at least one active electrode is a surface electrode arranged opposite the eyeball receiving portion, and wherein the reservoir has an internal wall, an external wall, and radial spacing fins between the internal wall and the external wall.

29. A device for transferring at least one active product into an eyeball by iontophoresis, comprising an annular reservoir configured to receive an active product, the reservoir having an eyeball receiving portion, at least one active electrode arranged in the reservoir, a passive electrode and a current generator, wherein one of the at least one active electrode is a surface electrode arranged opposite the eyeball receiving portion, and wherein the reservoir has an internal wall, an external wall, and spacing fins between the internal wall and the external wall, the spacing fins being curved and convex in a direction of an inlet for the active product.

30. A device for transferring at least one active product into an eyeball by iontophoresis, comprising a reservoir configured to receive an active product, the reservoir having an eyeball receiving portion, at least one active electrode arranged in the reservoir, a passive electrode and a current generator, wherein one of the at least one active electrode is a surface electrode arranged opposite the eyeball receiving portion, and wherein the reservoir defines a central space, the central space being closed off on an external side thereof by a transparent diaphragm configured to depressurize the central space.

\* \* \* \* \*

(12) EX PARTE REEXAMINATION CERTIFICATE (5165th)
United States Patent
Parel et al.

(10) Number: US 6,154,671 C1
(45) Certificate Issued: Jul. 26, 2005

(54) DEVICE FOR THE INTRAOCULAR TRANSFER OF ACTIVE PRODUCTS BY IONTOPHORESIS

(75) Inventors: Jean-Marie Parel, Miami Shores, FL (US); Francine Behar, Paris (FR)

(73) Assignee: Optis France, Paris (FR)

Reexamination Request:
No. 90/006,532, Jan. 28, 2003

Reexamination Certificate for:
Patent No.: 6,154,671
Issued: Nov. 28, 2000
Appl. No.: 09/225,206
Filed: Jan. 4, 1999

(30) Foreign Application Priority Data

Jan. 5, 1998 (FR) ............................................ 98 00009

(51) Int. Cl.⁷ .......................... A61N 1/30; A61M 31/00
(52) U.S. Cl. ........................................ 604/20; 604/521
(58) Field of Search .......................... 604/19–22, 501, 604/521, 289, 294, 295, 298, 300, 301; 607/53, 54, 141, 115; 424/422–429

(56) References Cited

FOREIGN PATENT DOCUMENTS

RU          995783          2/1983

OTHER PUBLICATIONS

G.A. Kiselev et al., "Procedure for the Administration of Drugs in Gels to Ocular Tissues Through The Use of Electrophoresis" (includes both the Russian–language reference and an English translation thereof).

Ludwig Von Sallmann, "Iontophoretic Introduction of Atropine and Scopolamine Into the Rabbit Eye", pp. 711–719 (1943).

Oleg I. Lebedev, "Electrophoretic Trials in the Early Diagnosis of Primary Glaucoma" pp. 1–18 (1983), (includes both the Russian–language reference and an English language translation thereof).

Francine F. Behar–Cohen et al., "Iontophoresis of Dexamethasone in the Treatment of Endotoxin–Induced–Uveitis in Rats" vol. 65, pp. 533–545 (1997).

*Primary Examiner*—Nicholas D. Lucchesi (57) ABSTRACT

A device for transferring a medicament into the eyeball by iontophoresis. A reservoir holding the active product is applied to a patient's eye. The reservoir has at least one active surface electrode facing the eye tissue lying at the periphery of the cornea. The reservoir also has a return electrode and a current generator. The return electrode is in contact with the patient's partly closed eyelids.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–29 is confirmed.

Claim 30 is cancelled.

\* \* \* \* \*